United States Patent [19]
Hibino et al.

[11] 3,951,998
[45] Apr. 20, 1976

[54] BENZOTHIAZOLE DERIVATIVES

[75] Inventors: Toshihiko Hibino, Takarazuka; Yoshio Suzuki, Itami; Shigeru Okano, Kawani; Yoichi Hara, Toyonaka; Etsuro Sato, Takarazuka, all of Japan

[73] Assignee: Sumitomo Chemical Company, Limited, Osaka, Japan

[22] Filed: June 17, 1974

[21] Appl. No.: 480,311

[52] U.S. Cl. ..................... 260/306.6 R; 260/268 H; 260/293.57; 424/248; 424/250; 424/267; 424/270
[51] Int. Cl.² ................ C07D 277/72; C07D 295/08
[58] Field of Search .............. 260/306.6 R, 247.1 H, 260/268 H, 293.57

[56] References Cited
FOREIGN PATENTS OR APPLICATIONS
7,400,265    1/1974    Japan
345,162    7/1972    U.S.S.R.

OTHER PUBLICATIONS
Edwards, Chem. Abst. 79:32036p, (1973).

Hibino, Chem. Abst. 80:133421k (1974).

*Primary Examiner*—Lorraine A. Weinberger
*Assistant Examiner*—Michael Shippen
*Attorney, Agent, or Firm*—Wenderoth, Lind & Ponack

[57] ABSTRACT

Novel benzothiazole derivatives of the formula

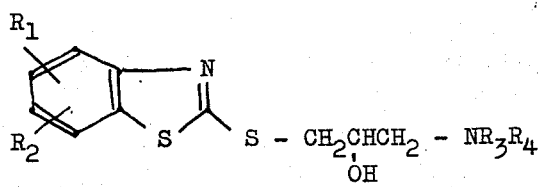

wherein $R_1$ and $R_2$ are individually hydrogen, lower alkyl, nitro, halogen, optionally substituted amino, carboxyl, lower alkoxy-carbonyl or di-lower alkyl-carbamoyl; and $R_3$ and $R_4$ are individually hydrogen, lower alkyl or α-lower alkyl-benzyl or $NR_3R_4$ is a saturated heterocyclic ring containing a nitrogen atom, and their salts. They are useful as antihypertensives.

6 Claims, No Drawings

BENZOTHIAZOLE DERIVATIVES

The present invention relates to benzothiazole derivatives and their preparation.

More particularly, this invention relates to novel compounds and their pharmaceutically acceptable salts, which are useful as antihypertensives, and to their preparation.

It is well known that some propanolamine-type compounds, for instance, propranolol, are applicable to the treatment of essential hypertension disease, but they have some disadvantages because they show strong $\beta$-adrenergic receptor blocking activity which is undesirable in the treatment of hypertension (J. Roba, G. Lambelin, and A. F. Deschepdryver Arch. int. Pharmacodyn. 200, 182 (1972); B. N. C. Prichard, and P. M. S. Gillman Am. J. Cardiol., 18, 387 (1966); and B. N. C. Prichard, and P. M. S. Gillman British Med. J. 1, 7 (1969) ).

As the result of the study seeking novel propanolamines which have excellent antihypertensive activity without showing any $\beta$-adrenergic receptor blocking activity, it has been found that, among various propanolamines, benzothiazole derivatives of the following formula (I) characteristically show excellent prolonged antihypertensive effect but no noticeable $\beta$-adrenergic receptor blocking activity, and they are useful as antihypertensives without any serious side effect:

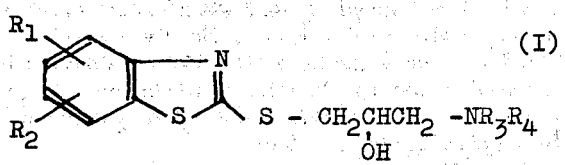

wherein $R_1$ and $R_2$ are individually hydrogen, lower alkyl, nitro, halogen, optionally substituted amino, carboxyl, lower alkoxy-carboxyl, or di-lower alkylcarbamoyl; and $R_3$ and $R_4$ are individually hydrogen, lower alkyl or $\alpha$-lower alkyl-benzyl or $NR_3R_4$ is a saturated heterocyclic ring containing a nitrogen atom.

Accordingly, an object of the present invention is to provide benzothiazole derivatives of the formula (I) and their pharmaceutically acceptable salts which are useful as antihypertensives.

Another object of the invention is to provide a process for producing said benzothiazole derivatives and their pharmaceutically acceptable salts.

A further object of the invention is to provide a pharmaceutical composition comprising an effective amount of at least one of such benzothiazole derivatives and/or their pharmaceutically acceptable salts and pharmaceutically acceptable carrier.

These and other objects of the invention will be apparent from the foregoing and subsequent description.

In the above mentioned formula (I), the term "lower alkyl" includes straight or branched alkyl having 1 to 4 carbon atom, for example, methyl, ethyl, n-propyl, iso-propyl, n-butyl, iso-butyl, sec-butyl and t-butyl. The term "halogen" includes bromine, fluorine, iodine and preferably chlorine. The term "optionally substituted amino" includes free amino and protected amino of which the protective group is $C_2 - C_5$ alkanoyl (preferably acetyl), benzylidene or $C_1 - C_4$ alkylsulfonyl substituted benzylidene (preferably p-methylsulfonyl-benzylidene). The term "lower alkoxy-carbonyl" includes $C_2 - C_5$ alkoxy carbonyl and preferably methoxycarbonyl. The term "saturated heterocyclic ring containing at least one nitrogen atom" means 5- or 6-membered saturated heterocyclic ring which may contain one or no other nitrogen or oxygen atom in addition to the required nitrogen atom. For example, pyrrolidino, piperidino, morpholino and piperazino are preferable.

The said pharmaceutically acceptable salts of said benzothiazole derivatives of the formula (I) may include organic or inorganic salts, for example, hydrochloric acid salt, sulfuric acid salt, phosphoric acid salt, tartaric acid salt, citric acid salt and mandelic acid salt.

According to the present invention, pharmaceutically preferred benzothiazole derivatives of the formula (I) defined above are those wherein $R_1$ and $R_2$ are each hydrogen or $C_1 - C_4$ alkyl and $NR_3R_4$ is $C_3 - C_4$ alkylamino and the most preferred are those wherein $R_1$ and $R_2$ are each hydrogen or methyl and $NR_3R_4$ is isopropylamino or t-butylamino, but the present invention is not limited to these.

According to the present invention, the benzothiazole derivatives of the formula (I) are prepared by reacting an aminoalcohol of the formula (II),

wherein $R_3$ and $R_4$ have the same meanings as defined above and X is halogen with a 2-mercaptobenzothiazole derivative of the formula (III),

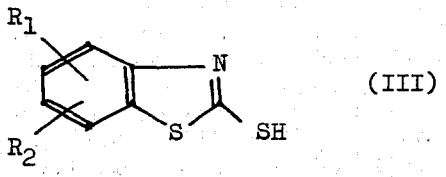

wherein $R_1$ and $R_2$ have the same meanings as defined above.

More particularly, the benzothiazole derivatives of the formula (I) are prepared by reacting a 2-mercaptobenzothiazole derivative of the formula (III) in a solvent in the presence of a base. As the solvent used in the above reaction, there are included water and organic solvents such as alcohol (for example, methanol, ethanol, n-propanol, iso-propanol, n-butanol, sec-butanol, t-butanol, amyl alcohol), dioxane, tetrahydrofuran, dimethylacetamide, dimethylformamide, dimethylsulfoxide, benzene, toluene, xylene and aqueous organic solvents described above, and other mixed solvents. As the base used in the above reaction, there are included inorganic bases such as sodium hydroxide, potassium hydroxide, calcium hydroxide, barium hydroxide, lithium hydroxide, lithium carbonate, sodium carbonate, calcium carbonate, barium carbonate, sodium bicarbonate, potassium bicarbonate, and organic bases such as pyridine, triethylamine, quinoline, and metal hydride such as lithium hydride, sodium hydride, potassium hydride, calcium hydride. The amount of the base is preferably more than 1 equivalent amount of 2-mercaptobenzothiazole (I) or aminoalcohol (II).

The reaction is conducted below 100°C., and it is preferably carried out below 30°C. in order to avoid polymerization and undesirable side reaction. And, in addition, the reaction is preferably carried out under an atmosphere of nitrogen in order to avoid oxidation of the aminoalcohol.

Commercially, the benzothiazole derivatives of the formula (I) are advantageously prepared by the above process. However, they are also prepared by reacting a 2-(2′,3′-epoxypropylthio)benzothiazole derivative of the formula (IV), $$\underset{R_2}{\overset{R_1}{\underset{|}{\diagdown}}} \begin{array}{c} N \\ \diagdown \diagup \\ S \end{array} SCH_2\overset{O}{\overset{/\backslash}{CHCH_2}} \qquad (IV)$$

or 2-(3′-halogeno-2′-hydroxypropylthio)benzothiazole derivative of the formula (V), $$\underset{R_2}{\overset{R_1}{\underset{|}{\diagdown}}} \begin{array}{c} N \\ \diagdown \diagup \\ S \end{array} \underset{SCH_2\overset{|}{CHCH_2}X}{\overset{OH}{}} \qquad (V)$$

(X : halogen)

with an amine of the formula (VI), $$HNR_3R_4 \qquad (VI)$$

wherein $R_1$, $R_2$, $R_3$ and $R_4$ are as defined above.

The reaction is carried out in a sealed tube or in an organic solvent such as alcohol (for example, methanol, ethanol, propanol), dioxane, dimethylsulfoxide, dimethylformamide, dimethylacetamide, acetone and is conducted at a temperature from 30° to 150°C. In this case, 2-(2′,3′-epoxypropylthio)-benzothiazole derivatives and 2-(3′-chloro-2′-hydroxypropylthio)-benzothiazole derivatives are prepared by reacting 2-mercaptobenzothiazole derivatives with epichlorohydrin in the presence of base.

The 2-mercaptobenzothiazole derivatives of the formula (III) are prepared by reacting o-halogenonitrobenzene derivatiaves with carbon disulfide and hydrogen sulfide according to the method by E. D. Amustutz, J. Amer. Chem. Soc. 68, 498 (1948), J. Teppema, L. B. Sebrell, J. Amer. Chem. Soc. 49, 1748 (1926), L. B. Sebrell, J. Amer. Chem. Soc. 45, 2391 (1923).

The benzothiazole derivatives thus obtained and their salts can be isolated and refined by a conventional procedure such as extraction, recrystallization, reprecipitation, column chromatography, or treatment with active carbon powder, and can be converted to pharmaceutically acceptable salts with inorganic or organic acid (for example, hydrochloric acid, sulfuric acid, phosphoric acid, tartaric acid, citric acid, mandelic acid) according to a conventional procedure.

Benzothiazole derivatives of the formula (I) and salts thereof may be brought into a suitable form such as tablet, powder, capsule, solution, injection or emulsion for administration according to the conventional method and may be administrated orally or parenterally.

The usual dosage of benzothiazole derivatives of the present invention is within a range of 10 mg/day to 1000 mg/day.

In order to illustrate the invention in detail, the following Examples are given, but are not by way of limitation.

EXAMPLE 1

2-(3′-isopropylamino-2′-hydroxypropylthio)benzothiazole.

Eight grams of 2-mercaptobenzothiazole was dissolved in 100 ml. of an equimolar aqueous sodium hydroxide solution, and to this solution 7.2 g. of 1-chloro-3-isopropylaminopropanol-2 in 50 ml. of methanol was added dropwise.

The reaction solution stood at room temperature overnight, and was extracted with chloroform after removal of excess methanol. The chloroform extract was dried over anhydrous magnesium sulfate and evaporated to give a yellowish oil, which was purified by column chromatography on alumina and followed by recrystallization from benzene-petroleum ether to give 6.0 g. of 2-(3′-isopropylamino-2′-hydroxypropylthio)-benzothiazole; mp 95° - 96°C.

$C_{13}H_{18}ON_2S_2$:
Anal. calcd. for
C; 55.31%, H; 6.43%, N; 9.93%, S; 22.67%;
Found :
C; 55.10%, H; 6.48%, N; 10.09%, S; 22.75%

EXAMPLE 2

5-methyl-2-(3′-isopropylamino-2′-hydroxypropylthio)-benzothiazole hydrochloride.

Eight grams of 5-methyl-2-mercaptobenzothiazole was dissolved in 130 ml. of an equimolar acqueous sodium hydroxide solution and to this solution, 5.5 g. of 1-chloro-3-isopropylaminopropanol-2 in 50 ml. of methanol was added dropwise.

After addition of 100 ml. of methanol, the reaction $$\underset{R_2}{\overset{R_1}{\diagdown}}\begin{array}{c}-NO_2\\-X\end{array} + CS_2 + H_2S \longrightarrow \underset{R_2}{\overset{R_1}{\diagdown}}\begin{array}{c} N \\ \diagdown \diagup \\ S \end{array} SH$$

And aminoalcohol derivatives of the formula (II) are prepared by reacting halogenohydrin with a suitable amine according to the method by V. R. Caertner, Tetrahedron, 23, 2123 (1967).

solution stood at room temperature overnight and was condensed to a half volume to extract with chloroform. The chloroform extract was dried over anhydrous magnesium sulfate and evaporated to give an oil, which was dissolved in benzene-chloroform and treated with dry gaseous hydrogen chloride. Precipitated white crystals were collected and recrystallized from acetone-ethanol to give 5.6 g. of 5-methyl-2-(3'-isopropylamino-2'-hydroxypropylthio)benzothiazole hydrochloride; mp 147° – 149 °C.

$C_{14}H_{20}ON_2S_2.HCl$:
Anal. calcd. for
C; 50.52%, H; 6.36%, N; 8.42%, S;19.23%;
Found: C; 50.40% H; 6.20%, N;
C; 8.36%, S; 19.02%

EXAMPLE 3

5-methyl-2-(3'-t-butylamino-2-hydroxypropylthio)-benzothiazole hydrochloride.

Eight grams of 5-methyl-2-mercaptobenzothiazole was dissolved in 150 ml. of an equimolar aqueous sodium hydroxide solution and to this solution, 1-chloro3-t-butylaminopropanol-2 in 50 ml. of methanol was added dropwise under an atmosphere of nitrogen. Under the same atmosphere, the reaction solution stood at room temperature overnight and was extracted with chloroform after removal of excess methanol.

The chloroform extract was dried in vacuo to give a pale reddish oil, which was purified by column chromatography on basic alumina and converted to its hydrochloride by a usual method. The hydrochloride was recrystallized from acetone-methanol to give needles of 5-methyl-2-(3'-t-butylamino-2-hydroxypropylthio)-benzothiazole hydrochloride; mp 150° – 155°C.

$C_{15}H_{22}N_2OS_2.2HCl.H_2O$:
Anal. Calcd. for
C; 45.83%, H; 6.42%, N; 7.14%, S; 16.34%, Cl; 18.06%;
Found:
C; 45.92%, H; 6.71%, N; 6.93%, S; 16.23%, Cl; 17.70%

According to Example 3, the following compounds were synthesized.

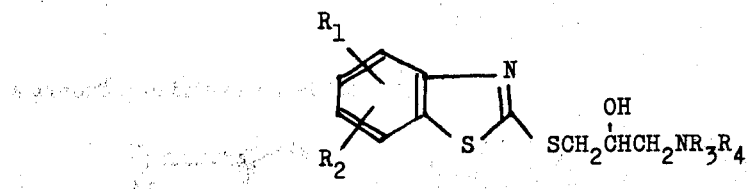

| Example No. | $R_1$ | $R_2$ | $R_3$ | $R_4$ | isolated form | physical const. |
|---|---|---|---|---|---|---|
| 4 | H | H | H | t-butyl | free amine | $n_d^{20}$ 1.5923 |
| 5 | $NH_2$ | H | H | iso-propyl | " | $n_d^{20}$ 1.6362 |
| 6 | $CH_3CONH$ | H | H | " | " | $n_d^{20}$ 1.5632 |
| 7 | $NO_2$ | H | H | " | " | $n_d^{20}$ 1.6135 mp 96–98°C. |
| 8 | Cl | H | H | " | " | (petroleum benzine) |
| 9 | $(C_2H_5)_2NCO$ | H | H | " | " | $n_d^{20}$ 1.5864 |
| 10 | ⌬-CH=N- | H | H | iso-propyl | free amine | mp 134–136°C. (acetone) |
| 11 | $CH_3SO_2$-⌬-CH=N- | H | H | " | " | mp 123–125°C. (benzene-pet. ether) |
| 12 | H | $CH_3$ | H | " | " | mp 102–104°C. (benzene-pet. ether) |
| 13 | Cl | $NH_2$ | H | " | " | mp 123–125°C. (benzene-pet. ether) |
| 14 | H | $CH_3$ | H | t-butyl | hydrochloride | mp 163–166°C. (acetone-methanol) |
| 15 | H | H | H | sec-butyl | free amine | mp 46–49°C. (ether-pet. ether) |
| 16 | COOH | H | H | iso-propyl | hydrochloride | mp 226°C. (decomp.) (acetone-methanol) |
| 17 | Cl | $NO_2$ | H | iso-propyl | free amine | $n_D^{20}$ 1.6061 |
| 18 | $CH_3OOC-$ | H | H | t-butyl | " | $n_D^{20}$ 1.5516 |
| 19 | H | H | H | α-methyl benzyl | " | $n_D^{20}$ 1.5825 |

| Example No. | R | isolated form | physical const. |
|---|---|---|---|
| 20 | pyrrolidino | free amine | $n_D^{25}$ 1.6095 |
| 21 | piperidino | " | $n_D^{25}$ 1.5945 |

EXAMPLE 22

A mixture of 10 g. of 5-methyl-2-(3'-chloro-2'-hydroxypropylthio)benzothiazole and 20 ml. of t-butylamine was heated at 100°C. in a sealed tube for 4 hours, and dried in vacuo to give a yellow oil, which was purified by column chromatography on basic alumina and converted to its hydrochloride by a usual method. This hydrochloride was recrystallized from acetone-methanol to give needles of 5-methyl-2-(3'-t-butylamino-2'-hydroxypropylthio)benzothiazole hydrochloride, mp 152° – 155°C.

What we claim is:

1. A compound selected from the group consisting of compounds of the formula

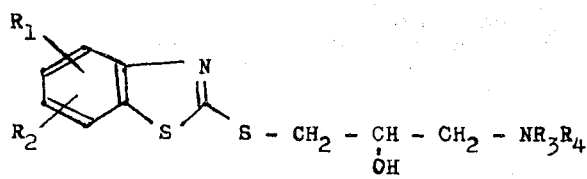

wherein $R_1$ and $R_2$ are individually hydrogen, lower alkyl, nitro, halogen, amino, $C_2 - C_5$ alkanoylamino, benzylideneamino, $C_1 - C_4$ alkylsulfonylbenzylideneamino, carboxyl, lower alkoxycarbonyl or di-lower alkyl-carbamoyl and $R_3$ and $R_4$ are individually hydrogen, lower alkyl or α-lower alkyl-benzyl, or $NR_3R_4$ is pyrrolidino, piperidino, morpholino or piperazino, and pharmaceutically acceptable salts thereof.

2. A compound according to claim 1, wherein $R_1$ and $R_2$ are individually hydrogen, $C_1 - C_4$ alkyl, nitro, chloro, amino, carboxyl, $C_2 - C_5$ alkoxy-carbonyl, di-$C_1 - C_4$ alkylsulfonylbenzylideneamino; and $R_3$ and $R_4$ are individually hydrogen, $C_1 - C_4$ alkyl, α-$C_1 - C_4$ alkyl-benzyl or $NR_3R_4$ is pyrrolidino, piperidino, morpholino or piperazino.

3. A compound according to claim 1, wherein $R_1$ and $R_2$ are hydrogen or $C_1 - C_4$ alkyl and $R_3$ and $R_4$ are $C_3 - C_4$ alkyl.

4. A compound according to claim 1, wherein $R_1$ and $R_2$ are hydrogen or methyl and $R_3$ and $R_4$ are hydrogen or $C_3 - C_4$ alkyl.

5. The compound of the formula

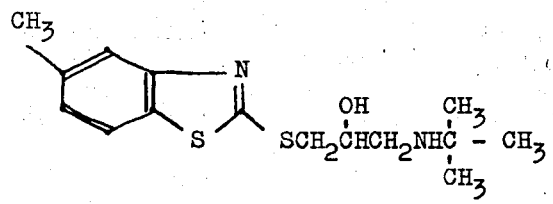

6. The compound of the formula

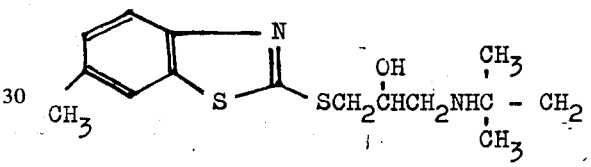

* * * * *